US00PP27296P3

(12) United States Plant Patent
Zaiger et al.

(10) Patent No.: US PP27,296 P3
(45) Date of Patent: Oct. 25, 2016

(54) PEACH TREE NAMED 'ICE ZEE'

(50) Latin Name: *Prunus persica*
Varietal Denomination: Ice Zee

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 133 days.

(21) Appl. No.: 14/544,567

(22) Filed: Jan. 23, 2015

(65) Prior Publication Data

US 2016/0219773 P1 Jul. 28, 2016

(51) Int. Cl.
*A01H 5/08* (2006.01)

(52) U.S. Cl.
USPC ..... Plt./195

(58) Field of Classification Search
USPC ..... Plt./195
See application file for complete search history.

*Primary Examiner* — June Hwu

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of large size fruit.
3. Fruit having a high degree of attractive red skin color.
4. Fruit with very good flavor and eating quality.
5. Fruit with firm flesh and good shipping quality.

1 Drawing Sheet

Botanical designation: *Prunus persica.*
Variety denomination: 'Ice Zee'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Snow Bliss' Peach (U.S. Plant Pat. No. 24,141) and our proprietary non-patented peach selections '62MA130', '99LH139' and '99LM526'.

STATEMENT REGARDING FEDERALLY SPONSORED RESEARCH AND DEVELOPMENT

Not applicable.

ORIGIN OF THE VARIETY

The new variety of peach tree (*Prunus persica*) was originated by us in our experimental orchard located near Modesto, Calif. as an open pollinated seedling selection from seed collected from our proprietary non-patented peach selection with the field identification number '62MA130'. The proprietary seed parent '62MA130' originated as a second generation seedling from the cross of our proprietary non-patented peach seedling selections '99LH139' and '99LM526'. A large number of these open pollinated seedlings were budded onto older established trees of 'Nemaguard' Rootstock (non-patented) to enhance earlier fruit production. Under close and careful evaluation we recognized the desirable tree and fruit characteristics and selected it in 2006 for additional asexual propagation and commercialization.

ASEXUAL REPRODUCTION OF THE VARIETY

In 2006 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous, upright growth and a productive and regular bearer of large size, white flesh, clingstone fruit. The fruit is further characterized by having very good flavor and eating quality and an attractive red skin color. In comparison to its immediate seed parent '62MA130' (non-patented) the fruit of the new variety has brighter red skin color and is approximately 6 days later in maturity. In comparison to 'Snow Bliss' Peach (U.S. Plant Pat. No. 24,141) the fruit of the new variety develops reddish pink color in the flesh as it matures compared to remaining white and the fruit is approximately 18 days earlier in maturity.

DESCRIPTION OF THE PHOTOGRAPH

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from an 8 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 8 year old specimens grown near Modesto, Calif., with color in accordance with Munsell Book of Color published in 1958.

Tree:

*Size*.—Large, usually pruned to 3 to 3.5 meters in height and width for economical harvesting of fruit, varies with different cultural practices.

*Vigor*.—Vigorous, growth of 1.5 to 2 meters in height the first growing season. Varies with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 6 consecutive years. No alternate bearing observed.

*Fertility*.—Self-fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 700 hours at or below 45° F.

Trunk:

*Size*.—Large. Average circumference 53.3 cm at 25.4 cm above ground on an 8 year old tree.

*Stocky*.—Medium stocky.

*Texture*.—Medium shaggy, roughness increases with age.

*Color*.—Varies from 2.5Y 7/2 to 2.5Y 5/2.

Branches:

*Size*.—Medium. Average circumference 11.4 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 37 in a 25.8 square cm section. Average length 3.4 mm. Average width 1.4 mm. Color varies from 7.5YR 5/10 to 10YR 6/10.

*Color*.—New growth varies from 2.5GY 6/8 to 5GY 6/6. Mature growth varies from 7.5YR 2/4 to 10YR 3/4, varies with age of growth.

Leaves:

*Size*.—Medium to large. Average length 129.9 mm. Average width 41.7 mm.

*Form*.—Lanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.2 mm. Average width 1.4 mm. Longitudinally grooved. Surface glabrous. Color 5GY 6/6.

*Glands*.—Type — reniform. Size — small to medium. Average length 1.1 mm. Average diameter 0.8 mm. Number varies from 2 to 4, average number 2. Located primarily on the base of the leaf blade and the upper portion of the petiole. Color 5GY 6/6.

*Stipules*.—Average number 2. Average length 7.5 mm. Edges — pectinate. Color 2.5GY 7/6.

*Color*.—Upper surface varies from 5GY 3/6 to 7.5GY 3/4. Lower surface 5GY 5/4. Midvein color varies from 2.5GY 7/6 to 5GY 7/6.

Flower buds:

*Size*.—Large. Average length 18.4 mm. Average diameter 11.2 mm.

*Hardiness*.—Hardy with respect to California winters.

*Density*.—Medium dense.

*Form*.—Plump, conical, becoming elongated before opening.

*Pedicel*.—Average length 5.1 mm. Average width 0.8 mm. Color varies from 2.5GY 6/6 to 2.5GY 5/6. Surface — glabrous.

*Color*.—Varies from 7.5RP 5/14 to 5RP 7/10.

Flowers:

*Blooming period*.—Date of First Bloom Feb. 22, 2014. Date of Petal Fall Mar. 2, 2014, varies slightly with climatic conditions.

*Size*.—Large, showy. Average height 21.0 mm. Average diameter 45.4 mm.

*Petals*.—Normally 5, alternately arranged to sepals. Size — large. Average length 19.6 mm. Average width 20.1 mm. Form — orbicular. Arrangement — free. Margin — sinuate. Petal apex — rounded. Petal base — rounded to somewhat truncated. Both surfaces glabrous. Color varies from 5RP 7/10 to 5RP 8/6, fades with age of flower.

*Sepals*.—Normally 5, alternately arranged to petals. Size — large. Average length 5.3 mm. Average width 5.3 mm. Shape — ovate, apex rounded to triangular. Margin — entire. Color — upper surface varies from 5R 2/4 to 7.5R 2/2. Lower surface varies from 5R 2/4 to 7.5R 2/2. Upper surface glabrous, lower surface pubescent.

*Stamens*.—Average number per flower 45. Average filament length 15.1 mm. On average, the stamens are above the height of the petals. Filament color varies from N 9.5/(white) to 5RP 7/6 depending on age of flower. Anther color varies from 10R 4/10 to 5Y 8/10.

*Pollen*.—Self-fertile. Color varies from 2.5Y 7/10 to 5Y 7/12.

*Pistil*.—Number — normally one. Surface pubescent. Average length 18.1 mm. Position of the stigma is even with the anthers. Color varies from 10Y 8.5/4 to 10Y 8/6.

*Fragrance*.—Moderate.

*Color*.—Varies from 5RP 8/6 to 2.5RP 8/4.

*Pedicel*.—Average length 5.1 mm. Average width 1.1 mm. Color varies from 2.5GY 6/6 to 2.5GY 5/6. Surface glabrous.

*Number flowers per flower bud*.—Normally one.

Fruit:

*Maturity when described*.—Firm ripe and ready for consumption.

*Date of first picking*.—Jun. 9, 2014.

*Date of last picking*.—Jun. 17, 2014, varies slightly with climatic conditions.

*Size*.—Large. Average diameter 70.4 mm. Average transversely in suture plane 75.9 mm. Average weight 258.4 grams, varies slightly with fertility of the soil, amount of thinning and climatic conditions.

*Form*.—Globose.

*Suture*.—Nearly smooth, extends from base to apex.

*Ventral surface*.—Smooth to very slightly lipped.

*Apex*.—Retuse.

*Base*.—Retuse.

*Stem cavity*.—Rounded to slightly elongated in suture plane. Average depth 5.7 mm. Average diameter 9.1 mm.

Stem:

*Size*.—Small. Average length 9.3 mm. Average diameter 2.2 mm.

*Color*.—Varies from 2.5GY 5/6 to 2.5GY 5/8.

Flesh:

*Ripens*.—Slightly earlier at the apex.

*Texture*.—Firm, meaty.

*Fibers*.—Few, small, tender.

*Firmness*.—Good, comparable to other commercial varieties.

*Aroma*.—Moderate.

*Amydgalin*.—Undetected.

*Eating quality*.—Very good.

*Flavor*.—Very good, mild, a good balance between acid and sugar.

*Juice*.—Heavy amount, enhances flavor.

*Brix*.—Average Brix 11.0°, varies slightly with amount of fruit per tree and climatic conditions.

*Pit cavity*.—Average length 39.2 mm. Average width 28.9 mm. Average depth 9.7 mm. Color 5Y 9/4.

*Color*.—Varies from 7.5Y 9/4 to 10Y 9/8 with 2.5R 5/10 bleeding in from the skin.

Skin:

*Thickness*.—Medium.

*Surface*.—Nearly smooth.

*Pubescence*.—Pubescent, short in length.

*Tendency to crack*.—None.

*Color*.—Ground color 7.5Y 9/4. Overspread with 5R 5/12 to 5R 2/4.

*Tenacity*.—Tenacious to flesh.

*Astringency*.—Undetected.

Stone:

*Type*.—Clingstone, strong adherence to flesh.

*Size*.—Large. Average length 38.5 mm. Average width 27.5 mm. Average thickness 18.8 mm.

*Form*.—Ovoid.

*Base*.—Flat.

*Apex*.—Pointed. Average length 1.3 mm.

*Surface*.—Pitted throughout, pits vary from round to elongated.

*Sides*.—Unequal, one side extending further from suture plane.

*Ridges*.—Relatively smooth, narrow ridges extending from base to apex.

*Tendency to split*.—None to very slight.

*Color*.—Varies from 7.5YR 6/6 to 10YR 6/8 when dry.

Kernel:

*Size*.—Medium to large. Average length 18.4 mm. Average width 11.9 mm. Average depth 5.3 mm.

*Form*.—Ovoid.

*Viability*.—Partially viable, some embryos with incomplete development.

*Skin color*.—Varies from 2.5Y 9/4 to 2.5Y 8.5/4.

Use: Dessert.

*Market*.—Local and long distance.

Keeping quality: Good, held firm in cold storage at 38° to 42° F. for 2 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peach tree, (*Prunus persica*) substantially as illustrated and described.

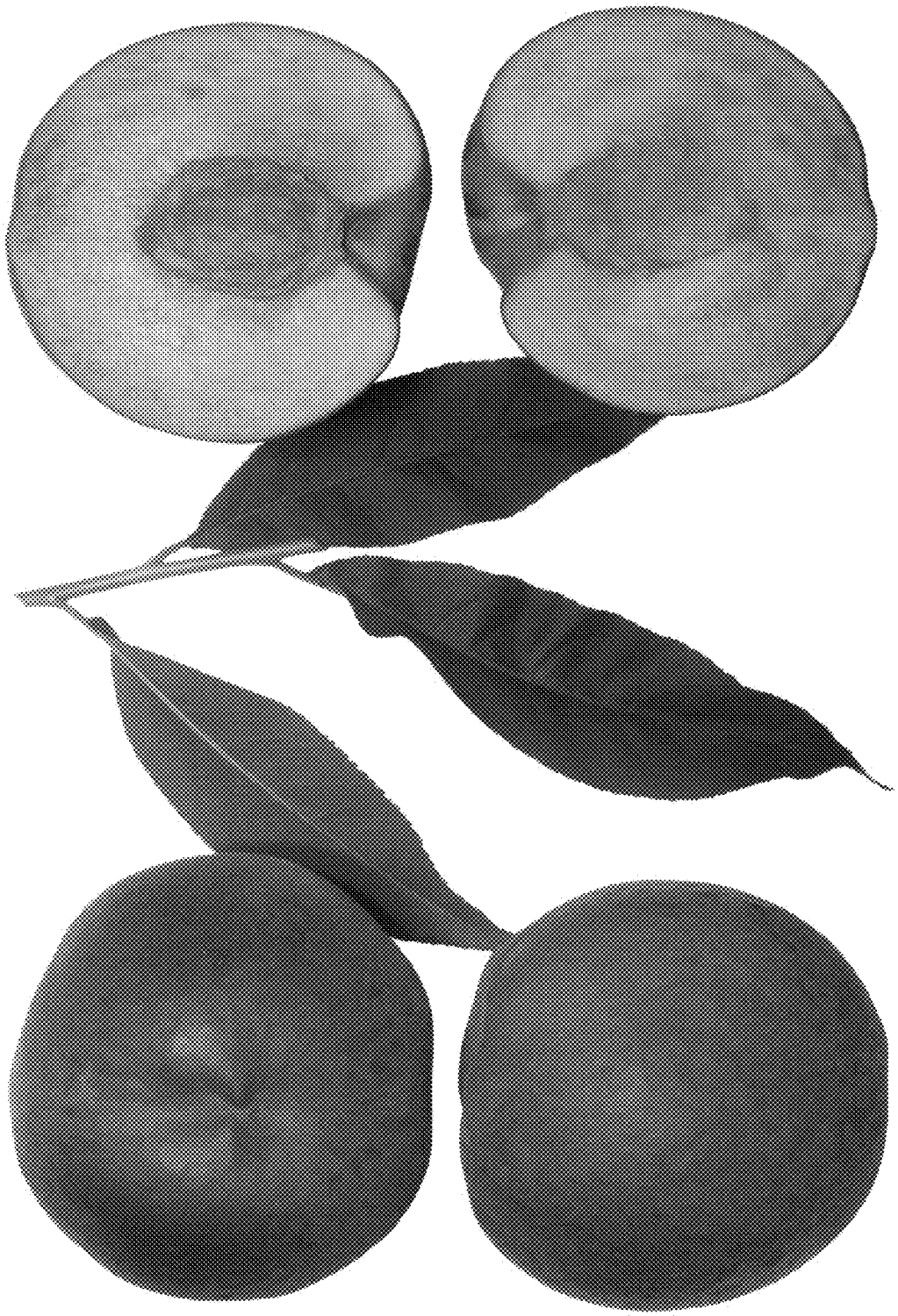

* * * * *